United States Patent [19]

Blake

[11] Patent Number: 4,515,348
[45] Date of Patent: May 7, 1985

[54] SKIN STAPLE EXTRACTOR

[76] Inventor: Joseph W. Blake, 88 Main St., New Canaan, Conn. 06840

[21] Appl. No.: 311,882

[22] Filed: Oct. 15, 1981

[51] Int. Cl.³ .............................................. B25C 11/00
[52] U.S. Cl. ....................................... 254/28; 227/63; 128/303 R
[58] Field of Search ........................... 227/63; 254/28; 128/303 R, 318; 81/9.5 R; 30/233

[56] References Cited

U.S. PATENT DOCUMENTS

| D. 271,742 | 12/1983 | Li et al. | D8/05 |
|---|---|---|---|
| 619,326 | 2/1899 | Merrill | 30/233 |
| 1,922,681 | 8/1933 | Heise | 254/28 |
| 2,202,984 | 6/1940 | Drypolcher | 254/28 |
| 2,967,303 | 1/1961 | Wise | 227/63 |
| 3,921,640 | 11/1975 | Freeborn | 128/318 |
| 4,026,520 | 5/1977 | Rothfuss et al. | 254/28 |

FOREIGN PATENT DOCUMENTS

| 0059778 | 9/1982 | European Pat. Off. | 254/28 |
|---|---|---|---|
| WO83/00428 | 2/1983 | PCT Int'l Appl. | 254/28 |

Primary Examiner—Henry J. Recla
Assistant Examiner—Karin M. Reichle
Attorney, Agent, or Firm—Charles J. Knuth; Peter C. Richardson; Harold W. Ordway

[57] ABSTRACT

A manually operable surgical staple extractor has a first handle element provided with a finger-receiving ring end and a second handle element also provided with a finger-receiving ring end. A first and second front portion of the extractor contain a slot and blade section parallel to an anvil and are pivotally connected by a rivet.

8 Claims, 6 Drawing Figures

SKIN STAPLE EXTRACTOR

BACKGROUND OF THE INVENTION

The present invention relates to a staple extractor, and more particularly to a manually operated extractor for surgical staples.

Surgeons are turning more and more frequently to the use of surgical staples, rather than conventional thread sutures, for closing wounds or incisions in the skin of a patient, because the stapling operation is often simpler. More important, however, is the fact that stapling is much faster than conventional thread suturing. Thus, particularly in those instances where a considerable amount of suturing is required, the length of time for the suturing operation and the length of time the patient must be maintained under anesthesia are greatly reduced when surgical staples are used.

Typical surgical staples are illustrated in U.S. Pat. Nos. 3,643,851 and 3,837,555. A staple of this type initially has an elongated crown terminating in a downwardly depending portion whose free ends are provided with downwardly and outwardly sloping cuts, forming points. During the forming and implanting of such a staple in the skin of a patient, end portions of the elongated crown are bent downwardly. This forms a staple with a narrower crown and L-shaped legs, the pointed ends of which are opposed.

The types of staple described above may be removed from the skin of a patient by bending the staple crown into a U-shaped configuration. This will cause the L-shaped legs of the staple to shift upwardly and outwardly so that they may be lifted from the patient's skin.

The prior art has proposed manual extractors for bending the crown of surgical staples and lifting the staple from the patient's skin. Typically, a prior art extractor comprises a pliers-like tool having first and second handle means pivoted together and formed of sheet metal. The first handle means terminates in a pair of anvils in parallel spaced relationship. The anvils are provided at their rearward ends with notches so that, when the anvils are slipped under the crown portion of a surgical staple, the crown will be received in the notches.

The second handle of the extractor generally is provided with a relatively thick, two-ply, blade-like forward end substantially as long or longer than the anvils. The anvils have projections extending towards one another to guide the blade-like forward end between them. When the handle elements of the extractor are in their open position, this blade lies above the anvils and the notches therein. As the handle elements are shifted to their closed position, the blade element passes between the anvils and the notches therein making the above described U-shaped bend in the staple crown located in the notches.

It is clear that when the anvils are slipped beneath the crown of a staple, they will rub against traumatized areas of the skin, causing pain to the patient. Since the blade is as long or longer than the anvils, it partially obscures the anvils, making their proper insertion under the staple crown and location of the staple crown in the anvil notches more difficult.

Another prior art manually operated surgical staple extractor has been proposed in U.S. Pat. No. 4,026,520 which is in the form of a pliers-like tool having first and second handle elements pivotally joined together near their forward ends. These handle elements are manually shiftable between open and closed positions and may be biased to their open position.

The first handle element is bifurcated at its forward end, the bifurcations terminating in a pair of elongated anvils in parallel spaced relationship. The forward ends of the anvils are angled toward each other with the front-most tips being contiguous or nearly so. At their rearward ends, the anvils are provided with aligned notches to receive the crown of a staple. The bifurcations of the first handle element provide a steep upwardly and rearwardly sloping surface adjacent each of the anvil notches to assist in and assure the location of a staple crown in the notches.

A thin blade means is located between the bifurcations of the first handle element and is operatively connected to the forward end of the second anvil element. The blade means has a nose portion shorter than the anvils and a lower edge adapted to produce a U-shaped bend in the crown of a staple located in the anvil notches. The blade nose portion is shiftable by the second handle element between a first position (when the handle elements are in their open position) wherein the lower edge of the nose lies above the anvils and the notches therein and a second position (when the handle elements are in their closed position) wherein the nose lies between the anvils with the lower edge of the nose located below the anvils.

The problem with this latter prior art construction is that it, also, does not overcome all of the earlier disadvantages.

For example, the front end portion of the anvils must be inclined and positioned with considerable precision in order to perform their intended purpose, i.e. to guide the blade as do the transverse anvil projections of the art prior thereto. The extractor must be urged to open position by a biasing means whose presence complicates the construction and may become dislocated, tending to jam the extractor. Also, the more or less planar finger-engaging portions of this tool do not offer very reliable assurance against slippage of the surgeon's fingers which may lead to slippage of the extractor, pulling on the staple and pain to the patient.

SUMMARY OF THE INVENTION

Accordingly, it is an object of the present invention to overcome the disadvantages of the prior art.

A more particular object of the invention is to provide a manually operable surgical staple extractor which is not possessed of the aforementioned disadvantages.

Still more specifically, it is an object of the present invention to provide an improved manually operated surgical staple extractor which is highly reliable in operation and simple in construction.

A concomitant object is to provide such a staple extractor in which the danger of slippage of the operator's (i.e. surgeon's) fingers on the tool is reliably prevented.

Yet an additional object is to provide such an extractor wherein there is no need at all for anvil formations which guide the staple extracting blade.

A further object of the invention is to provide an extractor of the type under discussion which may be made either as a single-use disposable tool (e.g. from synthetic plastic material) or as a sterilizable reusable tool (e.g. from metal or a combination of metal and sterilizable plastic).

Another object is to provide such an extractor which is inexpensive to produce.

In keeping with the above objects, and with still others which will become apparent hereafter, one aspect of the invention resides in a manually operable surgical staple remover which, briefly stated, may comprise a first handle element (may be of flat stamped-out sheet material) having a first rear portion provided with a finger-receiving ring end, and a first front portion of U-shaped cross-section and having a leading end provided at the bight of the U with a slot extending towards the first rear portion so as to define two parallel anvil sections; a second handle element (which may also be of flat stamped-out sheet material) having a second rear portion also provided with a finger-receiving ring end, and a second front portion provided with a blade section located between and parallel to the anvil sections and movable through the slot; the blade section terminating short of the front ends of the anvil sections; and rivet means pivotably connecting the second handle element to the first handle element within the confines of the U-shaped cross-section of the first front portion.

The invention wil hereafter be described with reference to an exemplary embodiment as illustrated in the drawing. However, it is to be understood that this is by way of explanation only and that the aspects for which protection are sought are set forth exclusively within the ambit of the appended claims.

DESCRIPTION OF PREFERRED EMBODIMENTS

Figure 1:
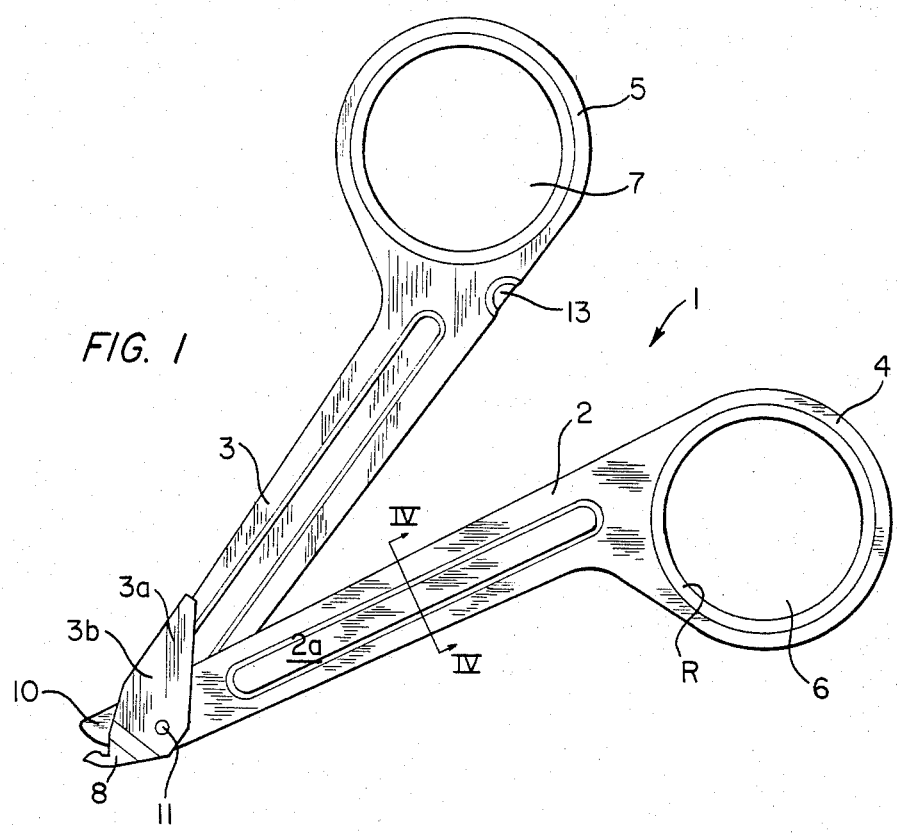
FIG. 1 is a side view showing the surgical staple remover according to the invention.
Figure 2:
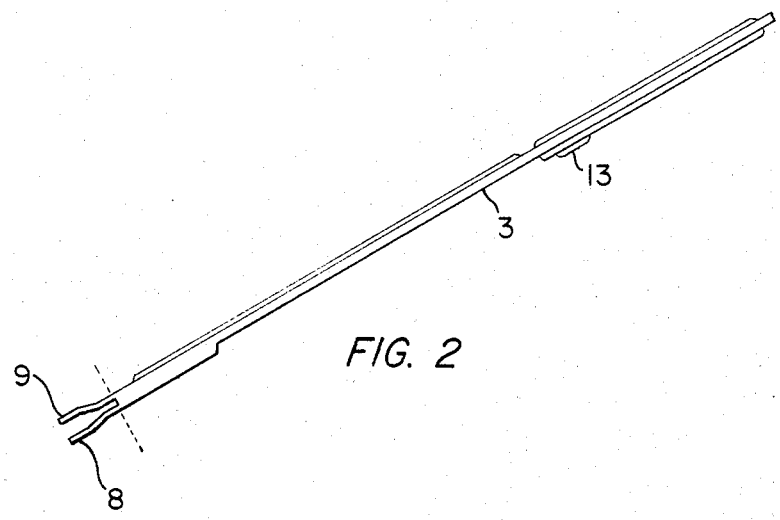
FIG. 2 is a top plan view.
Figure 3:
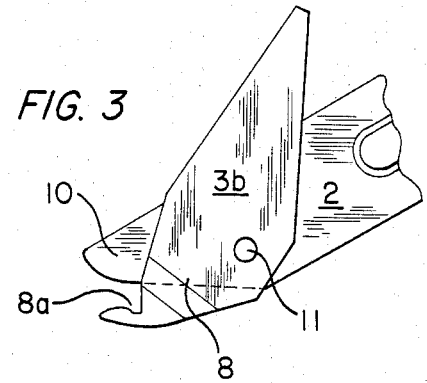
FIG. 3 is a detail view of one of the handle elements of FIG. 1.
Figure 4:
FIG. 4 is a section IV—IV of FIG. 1.

The staple remover 1 according to the invention is illustrated in FIGS. 1–6. It is of the scissors type, rather than of the prior-art pliers type and has two handle elements 2 and 3. The rear portions 4, 5 of these handle elements 2, 3 are bent over to form the finger-gripping eyelets 6, 7 of a pair of scissors. This eliminates the danger of finger slippage. Moreover, it eliminates the need for biasing means to bias the tool to open position since the surgeon is now able to manipulate the tool reliably and safely in the manner of a pair of scissors or forceps.

The leading portion 32 of the handle element 3 is bent from flat to U-shape so as to have two essentially parallel sides, of which only the side 3b is visible since the opposite side is not shown. These two sides form between themselves at their front ends a pair of strictly parallel anvils 8 and 9 (compare also FIG. 2) which have no portion inclined towards each other nor have projections extending towards each other.

The leading end portion of handle element 2 is configured as a staple extracting blade 10 which is located in strict parallelism between the anvils 8 and 9 without receiving any guidance from either of them. The anvils each have a notch 8a which is so shaped that it can receive a staple of either circular, oval or square cross-section.

In the space where the anvils 8, 9 are, the bight of the U-shaped portion 32 of handle element 3 is longitudinally slotted (FIG. 2), so that the lower edge of blade 10 can extend beyond the lower edge of anvils 8, 9. The handle elements 2, 3 are simply rivetted together at 11 to eliminate relative side-to-side motion that could adversely influence the accuracy of operation of the tool. The rivet 11 (see FIG. 3) is so located relative to the notches 8a that it prevents "rolling" of the staple being extracted.

Excess rotation of the handle elements is avoided by providing the lower edge of handle element 3 with the bent-up notch 13 in the path of movement of the lower handle element 2.

The extractor according to the invention may be made as a single-use, disposable tool from any suitable non-corrosive material or synthetic plastic material (the rivet 11 will probably always be of metal, for strength). When the tool is intended for sterilization and reuse, it may be made of stainless steel or the like, or a combination of such metal with an autoclavable synthetic plastic (known per se). In either case, the tool is well suited for pre-sterile packaging. Since it is made of stamped sheet metal, plastic ring R may be spring or otherwise secured in the finger-openings to protect the fingers of the user.

The manner of use of the inventive extractor is essentially the same as in the prior art and hence self-explanatory without requiring further details.

Figure 5:
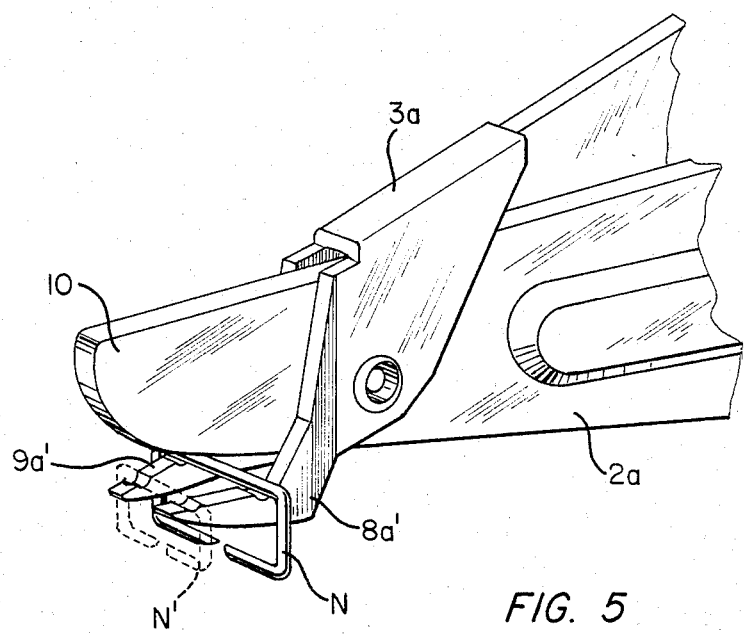
FIG. 5 is an enlarged detail of a modification.
Figure 6:
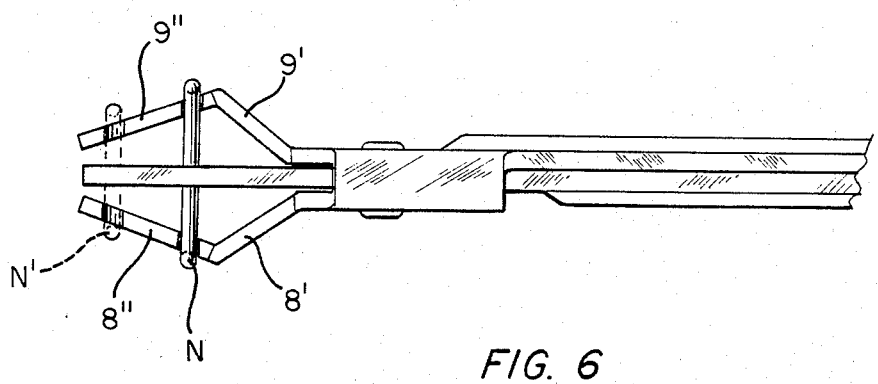
FIG. 6 is a top plan view of FIG. 5.

FIGS. 5 and 6 illustrate a modified embodiment in which the upper handle element 3a is formed with the two anvils 8a' and 9a'. Here it is the leading end portion of handle element 2a which is configured as a staple extracting blade 10.

A difference here is that the anvils 8a', 9a' do have mutually inclined portions 8', 8" and 9', 9". Each of the portions 8", 9" are provided with two staple-receiving notches N and N'. The purpose of the inclination and of the different notches, is to allow the remover to operate with standard staples of different sizes (as indicated by the showing of the smaller staple in broken lines in FIG. 5).

In all other respects, the remover of FIGS. 5 and 6 is similar to FIGS. 1–4 and therefore requires no further explanation.

The invention has hereinbefore been described with reference to exemplary embodiments. However, it is not intended to be limited thereto as modifications may be made in these embodiments without thereby departing from the spirit of the invention. Accordingly, the invention is to be considered authoritatively defined only in the appended claims.

I claim:

1. A manually operable extractor for surgical staples, comprising a first handle element having a first rear portion provided with a finger-receiving ring end, and a first front portion having a bifurcated forward end, said bifurcated forward end comprising first and second extensions of said first portion in overlapping parallel relationship to each other and separated by a space therebetween, a bight section joining said first and second extensions along one side thereof and extending parallel to a longitudinal edge of said first handle portion whereby said first and second extensions and said bight section define a U-shaped channel, said first and second extensions terminating in a pair of elongated anvil sections in parallel spaced relationship, said anvil sections having rearward ends with notches, and steep upwardly and rearwardly sloping edges from said notches to said bight section thereby defining a slot between said anvil sections; a second handle element having a second rear portion also provided with a finger-receiving ring end, and a second front portion terminating in a blade section, said second front portion pivotally mounted within said U-shaped channel of said first front portion with said blade section located between and parallel to said anvil sections and movable through said slot, said anvil sections being spaced apart throughout their length by a distance greater than the thickness of said blade section; rivet means for pivotably connecting said second handle element to said first handle element within said bifurcated forward end; and said finger-receiving ring ends comprising the sole means for spreading said rear portions of said handle elements apart and for bringing said rear portions toward each other.

2. An extractor as defined in claim 1, wherein said first and second handle elements are provided with cooperating engagement portions for limiting the extent to which said handle elements can be moved with respect to each other.

3. An extractor as defined in claim 1, wherein said handle elements and said rivet means connecting said handle elements are composed of stainless steel.

4. An extractor as defined in claim 1, wherein said handle elements and said rivet means connecting said handle elements are composed of sterilizable material.

5. An extractor as defined in claim 4, wherein said sterilizable material is metal.

6. An extractor as defined in claim 4, wherein said sterilizable material is part metal and part synthetic plastic material.

7. An extractor as defined in claim 1 for single use, wherein at least said handle elements are made of synthetic plastic material.

8. An extractor as defined in claim 1, wherein each of said handle elements is of one-piece construction.

* * * * *